United States Patent [19]

Cassels et al.

[11] Patent Number: 5,190,746
[45] Date of Patent: Mar. 2, 1993

[54] PLAQUE INHIBITING OLIGOSACCHARIDE

[75] Inventors: Frederick J. Cassels, Gaithersburg; Jack London, Rockville, both of Md.

[73] Assignee: The United States of America as represented by the Secretary of the Department of Health and Human Services, Washington, D.C.

[21] Appl. No.: 757,989

[22] Filed: Sep. 12, 1991

Related U.S. Application Data

[62] Division of Ser. No. 349,772, May 10, 1989, Pat. No. 5,071,977.

[51] Int. Cl.$^5$ .................. A61K 31/70; A61K 6/00
[52] U.S. Cl. ............................ 424/49; 536/123; 424/48; 424/50; 514/54
[58] Field of Search ............ 536/124, 123; 514/54; 424/48.50, 49

[56] References Cited

U.S. PATENT DOCUMENTS

| | | | |
|---|---|---|---|
| 3,931,398 | 1/1976 | Gaffar et al. | 424/92 |
| 3,993,747 | 11/1976 | Gaffar et al. | 424/88 |
| 4,217,341 | 8/1980 | Suddick et al. | 424/48 |
| 4,335,100 | 6/1982 | Robyt et al. | 424/48 |
| 4,353,891 | 10/1982 | Guggenheim et al. | 424/50 |
| 4,364,926 | 12/1982 | Yokogawa et al. | 424/50 |
| 4,731,245 | 3/1988 | Tsurumizu et al. | 424/92 |
| 4,737,359 | 4/1988 | Eigen et al. | 424/50 |
| 4,789,735 | 12/1988 | Frank et al. | 530/395 |
| 4,855,128 | 8/1989 | Lynch et al. | 424/49 |
| 4,950,604 | 8/1990 | Graber-Gubert et al. | 435/252.1 |
| 4,975,535 | 12/1990 | Masai et al. | 536/124 |

OTHER PUBLICATIONS

Dutton et al, Carbohydrate Research, 65 (1978) 251-263.
Watanabe et al, Carbohydrate Research 110 (1982) 170-175.
Bradbury et al, Carbohydrate Research, 122 (1983) 327-331.
Sarkar et al, Carbohydrate Research, 152 (1986) 205-215.
McIntire et al, Carbohydrate Research, 166 (1987) 133-143.
McIntire et al, Journal of Bacteriology, May 198, pp. 2229-2235.
Cassels et al, Journal of Bacteriology, Jul. 1989, pp. 4019-4025.
Cisar, Biochemistry 1990, 29, 234-248.
Cassels et al, The Journal of Biological Chemistry, vol. 265, #24, Aug. 25, 1990.
Kolenbrander et al, Infection and Immunity, Sep. 1990, pp. 3064-3072.
Kilian et al, International Journal of Systematic Bacteriology, Oct. 1989.
Cisar, Infection and Immunity, Jun. 1979, pp. 742-752.
Hawley et al, Antimicrobial Agents and Chemotherapy, Mar. 1980, pp. 372-378.
McIntire et al, Carbohydrate Research, 166 (1987) 133-143.

Primary Examiner—Johnnie R. Brown
Assistant Examiner—Nancy S. Carson
Attorney, Agent, or Firm—Birch, Stewart, Kolasch & Birch

[57] ABSTRACT

A purified oligosaccharide consisting of a hexasaccharide with a native molecular weight of 959 which can be isolated from the cell walls of Streptococcus oralis. The oligosaccharide is able to significantly block the interaction between the human oral plaque bacteria Streptococcus oralis H1 and Capnocytophaga ochracea ATCC 33596. This purified oligosaccharide contains saccharide components found to inhibit many know interactions between plaque bacteria and may be effective in prevention, inhibition and reversal of dental plaque deposits. The oligosaccharide may be applied effectively when incorporated in toothpastes, mouth wash, etc.

6 Claims, 6 Drawing Sheets

A B C D E F G

A B C D E F G H I J K L M N

A  B C  D

PLAQUE INHIBITING OLIGOSACCHARIDE

This application is a divisional of application Ser. No. 349,772, filed on May 10, 1989, now U.S. Pat. No. 5,071,977, the entire contents of which are hereby incorporated by reference.

BRIEF DESCRIPTION OF THE INVENTION

The present invention relates to a purified oligosaccharide which can be isolated from a natural source, e.g. from the cell wall polysaccharide of *Streotococcus oralis*. *S. oralis* is found in significant numbers in human dental plaque. This oligosaccharide is located at the site where a different oral plaque bacteria attaches, and contains saccharide components which are effective in blocking attachment of many plaque bacteria to each other. Use of this oligosaccharide may reverse the attachment of many plaque bacteria in the human oral cavity. For this use, the oligosaccharide is incorporated in tooth paste, mouthwash, etc. The *oligosaccharide* is a hexasaccharide with a molecular weight of 959.

BACKGROUND OF THE INVENTION

Most bacteria isolated from the human oral cavity possess the ability to participate in intergeneric coaggregation (bacteria from different genera bind to each other primarily via a protein on one attaching to a saccharide component on the other). Coaggregation is characterized by a highly specific binding between stable surface components found on two different bacterial types. Intergeneric coaggregation is thought to play an important role in the formation of dental plaque deposits (10, 11). *Streptococcus oralis* is one of the earliest colonizers of the clean tooth surface and is found in significant numbers in dental plaque (4, 19). The interaction between *Streptococcus oralis* H1 ATCC55229 and *Capnocytophaga ochracea* ATCC 33596 was first described by Kolenbrander and Andersen (9). A study (22) demonstrated that L-rhamnose and D-fucose were the most effective inhibitors of this coaggregation while galactosides, i.e. B-methyl galactoside, D-galactose, lactose and o-methyl galactoside were less effective inhibitors.

Thus far, the only bacterial carbohydrate receptor for a bacterial lectin studied in detail is the carbohydrate receptor on *Streptococcus oralis* 34 that is recognized by the adhesin on *Actinomyces viscosus* T14V. This interaction is inhibited by β-galactosides and B-N-acetylgalactosaminides. A cell wall coaggregation-inhibiting polysaccharide antigen from *Streptococcus oralis* 34 has been isolated and characterized (16). This polysaccharide consists of rhamnose, glucose, galactose and N-acetyl galactosamine in a hexasaccharide repeating unit (15). The polysaccharide inhibits coaggregation, contains saccharide components that by themselves are effective inhibitors of the interaction, and is a major cell surface antigen (16).

The available technology in combating dental plaque comprises the use of toothpastes, mouth washes, chewing gum, etc., which all work in a non-specific fashion, primarily by means of detergents and abrasives.

DETAILED DESCRIPTION OF THE INVENTION

The present invention works at the molecular level at the exact attachment site of two bacteria.

The present invention is based on the fact that an isolated and purified component of the cell wall polysaccharide from *Streotococcus oralis* H1 serves as a receptor for the adhesin on *Capnocytophaga ochracea* ATCC 33596. Criteria similar to those utilized in the studies of McIntire et al., (14, 16), i.e., the isolation of a polysaccharide antigen and its constituent oligosaccharide, which both inhibit coaggregation and contain monosaccharide components which serve as effective inhibitors of coaggregation, were applied to the identification and characterization of the *Streptococcus oralis* H1 carbohydrate receptor. The absence of this coaggregation-inhibiting polymer and its hexasaccharide repeating unit in a coaggregation-defective mutant of *Streotococcus oralis* H1 supported the conclusion that the polysaccharide isolated from the wild type strain was indeed the carbohydrate receptor.

An object of the present invention is to provide an novel oligosaccharide which can be isolated from the cell walls of *Streptococcus oralis* H1, said oligosaccharide consisting of a hexasaccharide of the structural formula I:

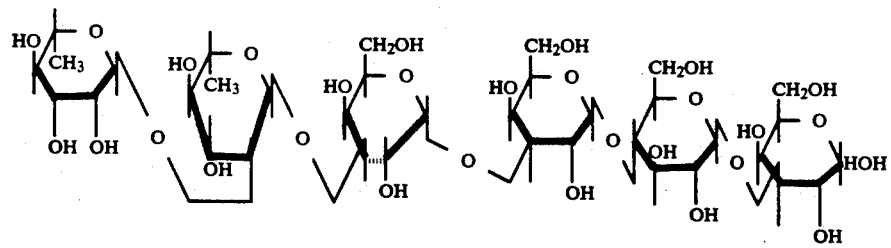

rha α|—72 rha α|—73 gal α|—73 gal B|—74
glc B|—73 gal
(rha=rhamnose; gal=galactose; glc=glucose)

A further object of the invention is to provide a process for the preparation of the above-defined hexasaccharide, said process comprises the steps of a) isolating crude cell walls of *Streptococcus oralis* H1 cells, b) liberating cell wall polysaccharide, c) optionally purifying the polysaccharide, d) hydrolysing the polysaccharide, e) isolating the desired product.

A further object of the invention is to provide a method of preventing, inhibiting or reversing the build-up of human dental plaque deposits by administering a composition comprising the hexasaccharide, a composition for preventing, inhibiting or reversing the build-up of human dental plaque deposits comprising the hexasaccharide, a method of inhibiting coaggregation between *Streptococcus oralis* H1 and *Capnocytophaga ochracea*, especially of the strain ATCC 33596, by preincubation of the hexasaccharide with the *C. ochracea* partner and finally a method for blocking the adhesin from the gram-negative bacteria *Capnocytophaga ochracea* by incubating the bacteria with the hexasaccharide.

As the oligosaccharide of the present invention appears to have excellent dental plaque prophylactic activities, it can be applied to human teeth for the purpose of the prevention of dental plaque by conventional methods, conventional types of unit dosages or with conventional carriers or diluents. A preferred composition is a tooth paste or a mouth wash. The conventional carriers or diluents are, for example, water, tooth powder, toothpaste, chewing gum, ointment, and the like. The hexasaccharide of the present invention is incorporated into the compositions in an amount of 0.001 to 5% by weight, preferably 0.05 to 1% by weight.

In the preparation of toothpaste and tooth powder containing the present hexasaccharide, conventional vehicles are used unless they give essentially undesirable effects to the activity of the hexasaccharide. An appropriate water-insoluble polishing agent can be incorporated in the toothpaste and tooth powder. Suitable examples of the polishing agents are dicalcium phosphate, tricalcium phosphate, and the like. These polishing agents usually constitute a major proportion by weight of the solid ingredients. The content of the polishing agents is preferably about 30 to 60% by weight of the total composition in toothpaste and 85 to 95% by weight in tooth powder.

In the preparation of toothpaste, some plasticizers may also be added. Suitable examples of plasticizers are water, glycerin, sorbitol, propylene glycol, monoglyceryl stearate, white petroleum jelly, cetyl alcohol, and the like, or a mixture thereof. The toothpaste is preferably formulated with a gelling agent, such as sodium carboxymethyl cellulose, hydroxyethyl cellulose, polyvinyl pyrrolidone, gum tragacanth, and the like, and may also optionally be formulated with other additional components, such as flavors, sweetening agents and coloring agents.

In the preparation of chewing gum containing the present hexasaccharide, conventional gum base such as chicle resin, polyvinyl acetate, and the like may be used. The chewing gum may also be formulated with other conventional vehicles, such as plasticizers, softeners, sweetening agents, flavors and coloring agents.

Other means for using the present hexasaccharide is a form of ointment. To the teeth to be treated an ointment containing the present hexasaccharide is applied, whereafter the teeth are being rubbed by a finger or a toothbrush. The ointment can be prepared by conventional method using conventional vehicles which can be applied to the mouth unless they show inhibitory or destructive action onto the present hexasaccharide. Suitable examples of materials to be used as an ointment base are sodium carboxymethyl cellulose, hydroxyethyl cellulose and Plastibase 50 W (dental paste base made by Squibb Co., Ltd.) which can form a jelly-like or creamy ointment.

The present hexasaccharide can also be used in the form of a chewable tablet or troche. When the chewable tablet or troche containing the present hexasaccharide is kept in the mouth, the hexasaccharide will be in contact with teeth for a long period of time. The chewable tablet or troche can be prepared by conventional methods using conventional vehicles, such as mannitol and sorbitol, and other conventional lubricating agents, sweetening agents, coloring agents, and the like.

The present hexasaccharide may also be admixed with confectionary such as candy, cake, and the like.

The hexasaccharide which blocks the coaggregation between *Streptococcus oralis* H1 and *Capnocytophaga ochracea* can be released from the walls of the gram-positive streptococcus cells by means of two methods, autoclaving and mutanolysin treatment, the latter has proved to be significantly more effective, ultimately yielding 2 to 3 fold higher quantities of purified material. For convenience, the two methods are designated below as AC (autoclaving) and ML (mutanolysin); the latter has two variants, I and II, so that the two mutanolysin-based variants are designated ML-I and ML-II, respectively. The methods are explained in detail in the section "Materials and Methods". The polysaccharide released from the streptococcal cell walls by either treatment yield the oligomer, which is present as repeating units of hexasaccharide, consisting of three hexoses, rhamnose, galactose and glucose, in the ratio of 2:3:1, respectively. The hexasaccharide units in the polysaccharide appear to be linked to one another by phosphodiester bonds. The purified hexasaccharide is a four fold more potent inhibitor of coaggregation than the native polysaccharide. Studies with a coaggregation-defective mutant of *Streptococcus oralis* H1 revealed that the cell walls of the mutant contained neither the polysaccharide nor the hexasaccharide repeating unit. The purification of a polysaccharide and its hexasaccharide repeating unit which both inhibited coaggregation and the absence of this polysaccharide or hexasaccharide on a coaggregation-defective mutant demonstrate that the hexasaccharide derived from the polysaccharide functions as the receptor for the adhesin from *Capnocytophaga ochracea* ATCC 33596.

MATERIALS AND METHODS

All cells from the bacteria *Streotococcus oralis* H1 and *Capnocytophaga ochracea* ATCC 33596 were grown under anaerobic conditions. *Streotococcus oralis* H1 was grown in a complex medium containing tryptone, yeast extract, Tween 80 and $K_2HPO_4$ with 0.3% glucose (17), and *Capnocytophaga ochracea* ATCC 33596 was cultivated in Schaedler broth (BBL, Microbiology Systems). A coaggregation-defective mutant of *Streotococcus oralis* H1, *Streotococcus oralis* PK1831, was provided by Dr. E. Weiss (Tel Aviv University, Israel).

Coaggregation-inhibition assays. Coaggregation assays with intact cells of *Streotococcus oralis* H1 and Capnocytophaga ochracea ATCC 33596 were conducted as described in (5). Initial screening for coaggregation-inhibiting material removed from *Streptococcus oralis* H1 cells was done using a semiquantitive microtiter plate assay. Twenty $\mu$l of two fold serial dilutions of the potential inhibitor in coaggregation buffer (1 mM Tris, 0.1 mM $CaCl_1$, 0.1 mM $MgCl_2$, 0.15 M NaCl, 0.02% $NaN_3$, pH 8.0) was placed into 96 well microtiter plates (Falcon, B-D, Oxnard, CA) and equal volumes of *Capnocytophaga ochracea* ATCC 33596 (at a cell density of about $1 \times 10^9$ cells/ml, 260 Klett units, red filter, Klett-Summerson, New York, NY) were added. After gentle vortex-mixing, the plates were incubated at room temperature (45 min). An equal volume of *Streptococcus oralis* H1 at the same cell density was added, gently vortex-mixed, incubated for 30 min and visually scored for the degree of coaggregation with the aid of a microtiter plate illuminator (Dynatech, Alexandria, VA). The half maximal inhibitory concentration was defined as that amount of inhibitor required to reduce coaggregation by 50% of the control value (buffer substituted for inhibitor). Quantitative inhibition assays were carried out according to the procedure described in Weiss et al. (22). To verify that the isolated coaggregation-inhibiting polysaccharide (CIP) was responsible for the observed inhibition, the purified polysaccharide was oxidized with 10mM sodium periodate at a pH of 4 for 1 hr at room temperature (13) and tested for its ability to inhibit coaggregation in the quantitative inhibition assay.

Chemical assays. Total hexose was assayed by the phenol-sulfuric acid method (7), inorganic and total phosphate by the method of Ames (1), protein was assayed by a dye-binding method (2), and nitrogen determination according to the method of Schiffman et al. (18).

Polysaccharide release from S. sanquis H1 cell walls. Polysaccharide was removed from S. oralis H1 cell walls in principle by two different methods as explained above, in the autoclaving (AC) and the mutanolysin methods (ML) of which the mutanolysin method has two variants, ML-I and ML-II. In both the AC and the ML-I methods the polysaccharide is purified, then the hexasaccharide is isolated from the hydrolysis products after the purified polysaccharide is degraded with hydrofluoric acid (HF). The ML-II method is similar to the ML-I method, but the purification of the polysaccharide is bypassed with the goal of obtaining only the hexasaccharide in high yield. The entire purification process can be summarized as having three stages:

Stage 1: Removal of the polysaccharide from the S. oralis cell wall

This is (in the AC method) effected by autoclaving (which is known to break the chemical bond between the bacterial cell wall and some cell wall polysaccharides, solubilizing the polysaccharides) and (in the ML-I and ML-II methods) by mutanolysin (an enzyme that cleaves the cell wall into small pieces, with the cell wall polysaccharide solubilized by the enzymatic action). The two mutanolysin methods, ML-I and ML-II, respectively, are identical in Stage 1. In Stage 1 the cell walls (in the AC method) or the whole cells (in both of the ML-methods) are washed with a detergent and an enzyme solution. As a detergent Triton can be used, as an enzyme Pronase can be used, the latter in a concentration of 0.05-1%, especially about 0.1-0.2%. In the ML methods the cells are advantageously washed with a strong salt solution in order to denature and remove adherent protein and lipid; an especially preferred salt solution is a quanidine hydrochloride solution in a strength of from 3 to 7 M, preferably at least 4 M, especially 6 M.

Stage 2: Purification of the polysaccharide from other components of the autoclaving- or mutanolysin-derived extract The purification of the polysaccharide from the AC or ML-I methods derived extract was accomplished by anion exchange chromatography (on a Mono Q column). Purity was demonstrated by immunoelectrophoresis of the polysaccharide with development of the electrophoresis gel with antibody to whole S. oralis H1 cells. The polysaccharide purification procedures for cell wall derived material extracted by AC and ML-I methods were identical. Stage 2 was bypassed in the ML-II method.

Stage 3: Purification of the hexasaccharide from the polysaccharide hydrolysate

In all three methods the hexasaccharide was purified by HPLC on an amino bonded silica column ($NH_2$ silica), and the purity demonstrated by HPTLC. The AC and ML-I methods in Stage 3 were identical. The ML-II method was different in that the mutanolysin extract from Stage 1 was treated with HF and the hexasaccharide purified from the hydrolysate of the total extract (instead of the hydrolysate of the polysaccharide).

The benefits of the ML-I method in relation to the AC method are a high yield of purified polysaccharide and subsequent hexasaccharide if desired, and this procedure provides a simple, effective way to scale up in order to isolate greater quantities of the purified materials.

The ML-II procedure provides a simple, highly efficient way to isolate purified hexasaccharide in milligram quantities with the least amount of effort of the three methods. This variation on the mutanolysin method is unique and constitutes a preferred variant of the process according to the invention.

The autoclaving method was based on the hydrolysis of the phosphodiester linkage between polysaccharide and peptidoglycan by exposure to high temperatures (3) and was a variation of that reported by McIntire et al. (16). Washed whole cells suspended in 25 mM Tris-HCl buffer, pH 8.0 were ultrasonically disrupted (Branson, 2 cycles of 6 min each, constant cooling) and the cell walls were obtained from the layer above the intact cell pellet following centrifugation ($25,000 \times g$ for 20 min). After washing, the isolated cell walls were treated with 0.1% Triton-X 100 (membrane purity grade, Boehringer Mannheim), in the Tris HCl buffer (16h, 4° C.), washed thoroughly in buffer without detergent, incubated in 0.2% Pronase (Calbiochem, La Jolla) dissolved in the Tris HCl buffer (two cycles of 2.5h, at 37° C.), and washed. The treated cell walls were then autoclaved in deionized water for 60 min at 6.8 kg/cm$^2$ pressure.

The second method, treatment with mutanolysin, (ML-I), has been employed successfully with S. oralis 34 (6). Intact S. oralis H1 cells were sequentially treated with 0.1% Triton X-100 in Tris HCl buffer (72 h, at 4° C.); 0.1% Pronase (Calbiochem) in Tris HCl buffer (two cycles of 2.5 h each at 37° C.); and 6M guanidine HCl for 48-72 h. at 4° C., with extensive washing after each treatment. This crude cell wall preparation was then digested by incubation with 26 μg/ml (corresponding to 4 mg/g initial wet weight S. oralis H1 cells) mutanolysin.

Cell wall material of the coaggregation-defective mutant were obtained by the mutanolysin method (equivalent to ML-I).

Isolation of coaggregation-inhibiting material. Material released from isolated S. oralis H1 cell walls by the autoclaving method was clarified by centrifugation at $25,000 \times g$ for 20 min followed by ultracentrifugation at $300,000 \times g$, for 90 min. More non-CIP material was removed by precipitation by lowering the pH to 1.5-2.0 with 4M HCl (16). The pH of the polysaccharide solution was readjusted to 6.0-6.5 with 4M NaOH, dialyzed against deionized water and lyophilized.

Polysaccharide released from crude cell walls by the mutanolysin method ML-I was clarified by centrifugation at $25,000 \times g$ for 20 min and the supernatant was adjusted to a concentration of 5% trichloroacetic acid (TCA) by the addition of 50% TCA. After centrifugation at 25,00033g for 20 min., the supernatant was neutralized by adding solid Tris, dialyzed extensively against water and lyophilized.

The autoclaving extract and the mutanolysin (ML-I and ML-II) extract were both assayed for their ability to inhibit coaggregation in a semiquantitive microtiter plate assay.

Hydrofluoric acid treatment. Solutions containing 10 mg/ml of crude polysaccharide preparation (from ML-II), purified polysaccharide (from AC and ML-I) or purified oligosaccharide (from AC, ML-I and ML-II) were treated with 48% hydrofluoric acid (HF, Baker) for 4 days at 4° C (23). HF was removed by 4 or 5 cycles of lyophilization or evaporation (Speed-Vac, Savant) followed by rehydration with distilled, deionized water. The rate and efficacy of hydrolysis was monitored by treating aliquots of purified polysaccharide with 48% HF for 30 min, 1 h, 4 h, 8 h, 24 h, 48 h, 72 h, 96 h, and 144 h in a time course experiment; HF was removed as above.

Isolation of S. oralis H1 CIP and HF released oligosaccharide. Coaggregation-inhibiting material released from S. sanguis H1 cell walls by both the autoclaving and the mutanolysin method ML-I was further purified by anion exchange chromatography on a Mono Q HR 5/5 FPLC column (Pharmacia) mounted on a Hewlett-Packard 1090L high performance liquid chromatograph (HPLC). Polysaccharide was eluted at a flow rate of 0.5 ml/min with a 0.1 to 0.25 M NaCl gradient prepared in 2 mM Tris-HCl, pH 8.0. All fractions were monitored for presence of neutral hexose by the phenol-sulfuric acid assay (7).

The oligosaccharides released by HF treatment of polysaccharide purified on the Mono Q column were separated from partially digested starting material by molecular sieve chromatography on a 2.4×90cm P2 column (BioRad) using distilled water as the eluent; the flow rate was 25 ml/h. Fractions from the P2 column were pooled, lyophilized, resuspended in a mixture (75%: 35%) of acetonitrile (ACN, Burdick and Jackson) and water (HPLC grade, Burdick and Jackson) and applied to 8 mm x 30 cm MicroPak AX-5 (Varian) diaminopropyl bonded silica HPLC column (24). The major oligosaccharide was eluted by passing a linear gradient of water through the column. The gradient was initiated after washing the column for 15 min with the initial ACN:water mixture; the gradient was formed by increasing the aqueous phase with 1.75% water/min. at a flow rate of 1 ml/min.

Gas-liquid chromatography. Oligosaccharide purified by HPLC was hydrolyzed with 4M trifluoroacetic acid (TFA) and the monosaccharides converted to their respective alditol acetate derivatives (8). Standards were purchased as alditol acetate derivatives (Biocarb, Lund, Sweden) or derivatized from monosaccharides (8). Samples and standards were analyzed by gasliquid chromatography (Hewlett-Packard, model 5840A) fitted with a capillary inlet system and flame ionization detector. A 0.25 mm ×15 cm SP2330 cyanopropyl bonded phase capillary column (Supelco) was used to resolve the alditol acetate derivatives of the monosaccharides. The injector and detector temperatures were held at 300° C. and the oven was maintained at a constant temperature of 220° C. The carrier gas, helium, was flushed through the column at a flow rate of approximately 2.5 ml/min.

High performance thin-layer chromatography. All samples including the CIP, HF released oligosaccharides, and monosaccharides derived from the HPLC purified oligosaccharide were applied to Silica 60 high performance thin-layer chromatography (HPTLC) 10×10 cm glass backed plates (EM Science, Cherry Hill, N.J.), and resolved using a mobile phase consisting of chloroform, methanol and water in a ratio of 10:10:3 (by volume) (21). Constituents in the samples were visualized by spraying the plates with a freshly prepared solution of naphthoresorcenol (20 mg), sulfuric acid (0.2 ml) and ethanol (10 ml) (12).

Immunoassays. Immunoelectrophoresis was carried out according to the method of Wang (20). A solution containing 1% agarose (electrophoresis grade, BRL) in barbital buffer was poured onto gelbond (FMC, Rockland, Maine) support medium and 15 µl samples containing roughly 5 µg of the appropriate preparation were loaded into wells and were subjected to electrophoresis. Troughs were filled with 150 µl antisera raised to whole, intact S. sanguis HI cells and allowed to develop. Gels were stained in 0.1% amido black.

RESULTS

Purification of coagregation-inhibiting polysaccharide (CIP). The materials released by mutanolysin treatment and by autoclaving were tested in a semiquantitative coaggregation-inhibition assay for their ability to prevent the interaction of the two partner cells and were analyzed for their chemical content. Half-maximal inhibition of coaggregation between the two partner cells took place at 4.0 mg/ml and 4.4 mg/ml for the mutanolysin extract and the autoclaving extract, respectively. The results are shown in Table I.

TABLE 1
INHIBITION ACTIVITY AND CHEMICAL ANALYSES OF AUTOCLAVING AND MUTANOLYSIN EXTRACTS AND ION EXCHANGE PURIFIED POLYSACCHARIDE RELEASED FROM Streptococcus oralis H1 CELL WALLS

|  | Inhibition[1] (mg/ml) | Hexose[2] (wt %) | Phosphate (wt %) | Nitrogen (wt %) |
|---|---|---|---|---|
| A. | | | | |
| Mutanolysin Extract | 4.0 | 81.6 | 6.3 | 2.5 |
| Peak 2a[3] | 1.7 | 86.7 | 8.8 | 0.7 |
| Peak 2b | 1.7 | 85.3 | 9.0 | 0.7 |
| B. | | | | |
| Autoclaving Extract | 4.4 | 84.5 | 7.1 | 1.9 |
| Peak 2a[4] | 1.7 | 82.6 | 8.6 | 0.5 |
| Peak 2b | 1.7 | 80.1 | 7.4 | 0.9 |

Figure 1A:
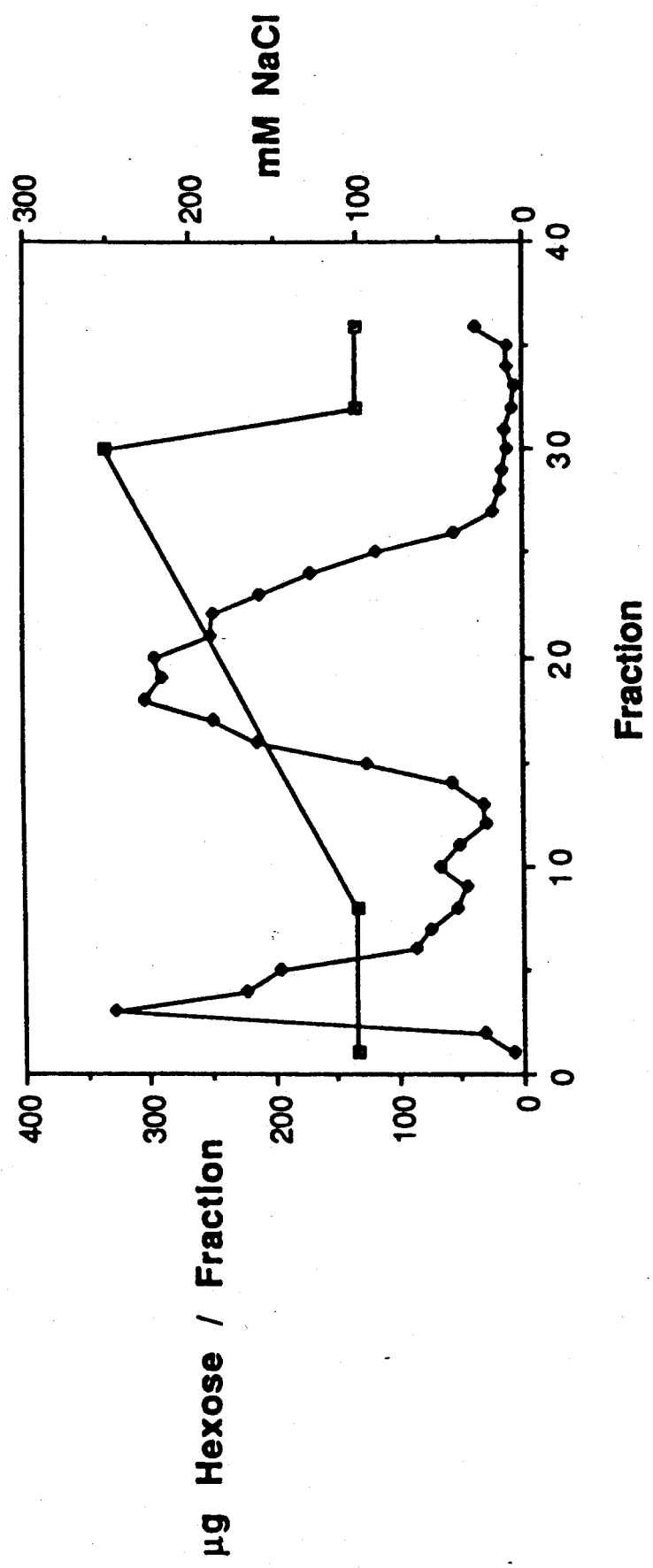
FIG. 1A and 1B. Elution profile and immunoelectrophoresis of selected fractions of polysaccharide (mutanolysin released coaggregation-inhibiting material) eluted from HPLC anion exchange chromatography. A) Lyophylized coaggregation-inhibiting material was resuspended in 2 mM Tris, 0.1M NaCl and applied onto a Mono Q anion exchange column. Coaggregation-inhibiting material was eluted with a salt gradient of 0.1–0.25M NaCl (♦-µg hexose/fraction; ▢-mM NaCl). B). Immunoelectrophoresis stained with 0.1% amido black. Numbers refer to fraction numbers of A). Troughs were filled with rabbit antisera to whole S. oralis H1 cells.

[1]Value range reported as approximate mg amount necessary to give half maximal inhibition in microtiter inhibition assay.
[2]Chemical assays as described in Materials and Methods. Phosphate was present as organic phosphate. Protein assays indicated that protein levels were below the level of detection in all samples (less than 0.5%).
[3]Peak 2a refers to fractions 15-20 and Peak 2b refers to fractions 21-27 in FIG. 1A.
[4]Peak 2a refers to fractions 16-21 and Peak 2b refers to fractions 22-29 from a column run under conditions identical to those of FIG. 1A.

When compared by chemical assays, only slight differences were found between the two preparations released from S. sanquis H1 cell walls. The materials consisted primarily of neutral hexose 81.6-84.5% by weight of initial lyophylized material), while organic phosphate was present in the range of 6.3 to 7.1%. The content of nitrogen was low (1.9-2.5%), and protein assays indicated no detectable protein.

Figure 1B:
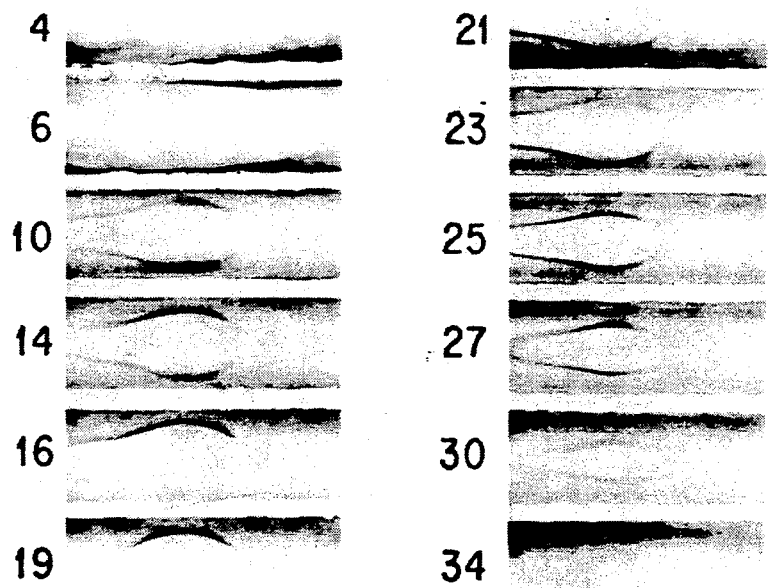

Polysaccharide released by either method was eluted from a Mono Q anion exchange chromatography by applying a NaCl gradient. The elution profiles for the mutanolysin extract (FIG. 1A) and the autoclaving extract (not shown) were very similar. In both instances, sugar-containing material was eluted with a NaCl concentration between 130-200 mM. Samples were taken from selected areas across the peak, subjected to immunoelectrophoresis (FIG. 1B), and developed with anti-S. oralis H1 serum to determine whether any of the fractions contained cell surface-associated antigens. Multiple immune precipitin arcs appeared in the initial flow-through material (Peak 1 of FIG. 1A, fractions 1-6) while the eluted material (Peak 2, fractions 15-27) consisted of a single antigen. While a single antigen was present in the salt-eluted peak (Peak 2) for both the mutanolysin-released material and the autoclaving-released material (not shown), the fractions comprising the peak were divided into two lots (forward, Peak 2a, and latter, Peak 2b, portions of the peak) and compared for inhibitory activity and chemical content, Table 1. Peak 2a was essentially the same as Peak 2b by all criteria tested, and the Mono Q purified mutanolysin extract (Peak 2a and 2b) appeared to be identical to the Mono Q purified autoclaving extract. Peak 2a and 2b polysaccharides were more effective inhibitors than the starting materials before ion exchange purification. The nitrogen detected in the assays did not appear attributable to protein and was most likely due to contaminating peptidoglycan.

CIP was released from cells irrespective of the method used, however losses of cell wall material occurred at several steps during the autoclaving protocol. For example, sonication failed to remove all of the wall material from cells and the first centrifugation step did not recover the smaller cell wall components. After autoclaving, larger particles of cell wall capable of agglutinating C. ochracea ATCC 33596 were removed only by ultracentrifugation. The losses that occurred during the early steps of the autoclaving procedure were not manifested in the mutanolysin method. The initial steps in the mutanolysin procedure removed much of the cell's protein and lipid components leaving a crude cell wall preparation (probably representing the peptidoglycan skeleton), prior to digestion by the muramidase. Recovery of CIP after mutanolysin treatment was 2-3 fold greater than with the autoclaving method (data not shown).

Subsequent studies were conducted with polysaccharide preparations derived by mutanolysin treatment.

Figure 2:
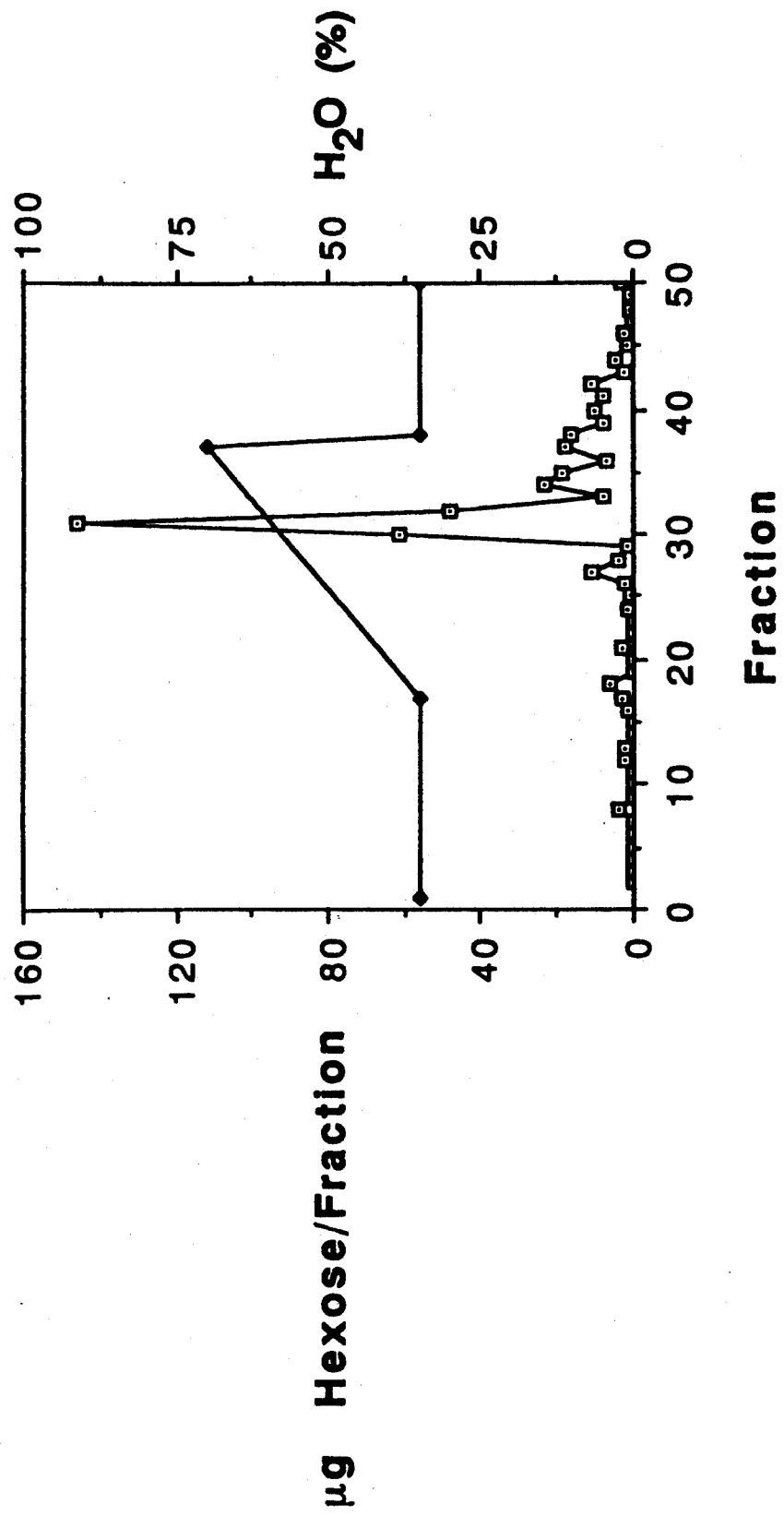
FIG. 2. Isolation of hydrofluoric acid released major oligosaccharide. P2 pooled, HF released material was applied to a MicroPac AX-5 HPLC column and eluted with a gradient of increasing water (▢-µg hexose/fraction; ♦-% H₂O). See Materials and Methods for chromatography conditions.
Figure 3:
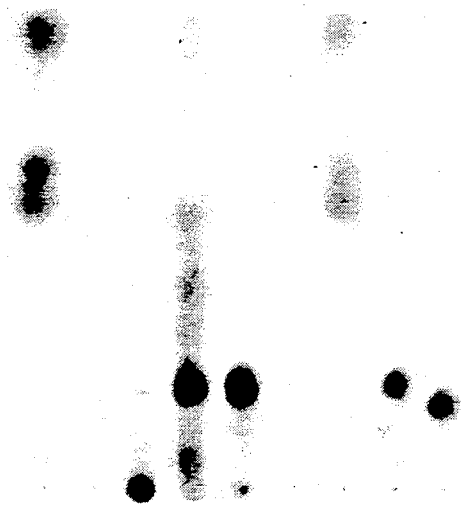
FIG. 3. HPTLC of CIP (B); HF treated CIP (C); HPLC purified oligosaccharide (D); and HPLC purified oligosaccharide hydrolyzed to monosaccharides (E) by trifluoroacetic acid (4M, 4h, 100° C) run on Silica G HPTLC. See Materials and Methods for chromatography conditions. Standards A) Equimolar mixture of rhamnose, glucose and galactose (fastest (top) to slowest migrating, respectively); F) maltopentaose; G) maltohexaose. 16 µg sample applied to lane C); all other 2–8 µg/lane.

Purification of HF released oligosaccharide. Anion exchange purified CIP was HF treated and passed over a P2 column to separate unhydrolyzed and partially hydrolyzed polysaccharide from lower molecular weight material (less than 2kD). The lower molecular weight material was pooled and applied to a MicroPak AX-5 HPLC column. The major oligosaccharide component was eluted at a ratio of approximately 60:40, water to ACN (FIG. 2). The oligosaccharide was resolved on Silica 60 HPTLC, and compared to the intact and HF treated polysaccharide (FIG. 3, B-D). The intact CIP (FIG. 3B) did not migrate from the origin under these chromatographic conditions; after treatment with HF (4d, 4° C.) the CIP was hydrolyzed to smaller components, with one prominent major oligosaccharide component (FIG. 3C). This component was isolated from the other hydrolysis products by HPLC (FIG. 3D). When compared to reference oligosaccharides, maltopentaose and maltohexaose (FIG. 3F and 3G, respectively), the major oligosaccharide migrated with a mobility between the two standards, suggesting that this oligosaccharide was either a pentasaccharide or hexasaccharide. When the purified oligosaccharide was hydrolyzed with TFA and resolved by HPTLC (FIG. 3E), three hexose components were resolved which comigrated with the reference standards rhamnose, galactose, and glucose (FIG. 3A).

Figure 4:
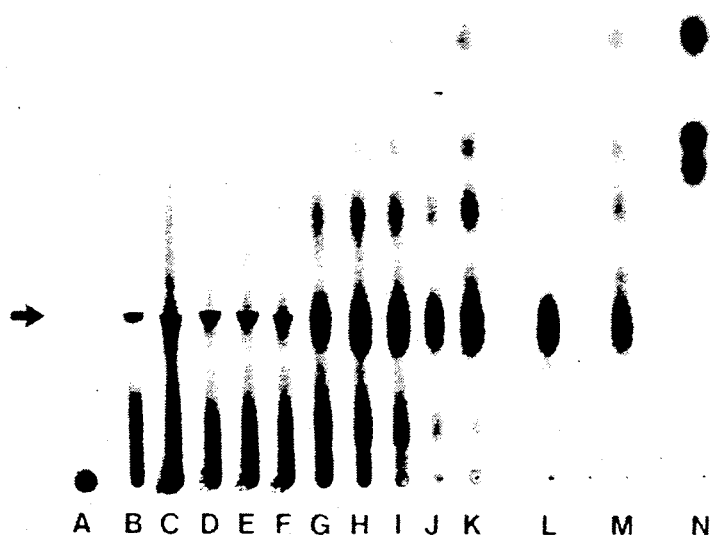
FIG. 4. HPTLC of HF treated CIP in a time course experiment, and the purified oligosaccharide after HF treatment. (A) CIP; HF treated CIP in time course experiment (B-K; 0.5, 1, 2, 4, 8, 24, 48, 72, 96, and 144 hours, respectively). (L) HPLC purified oligosaccharide (M) HPLC purified oligosaccharide after HF treatment (4d, 4° C); N) Equimolar mixture of rhamnose, glucose and galactose. Arrow indicates position of the major oligosaccharide component.

Hydrolysis of Polysaccharide and purified oligosaccharide. In a time course experiment extending from 30 min to 6 days, hydrolysis of the purified CIP (FIG. 4A) gave rise to one discrete oligosaccharide component (denoted by arrow) and large amounts of partially hydrolyzed polysaccharide after only 30 min incubation (FIG. 4B). With increasing length of HF exposure, more of the non-migrating CIP was hydrolyzed to the major oligosaccharide, and components smaller and faster migrating than the major oligosaccharide became more prominent (FIG. 4 C-K; as compared to monosaccharide standards, FIG. 4N). To maximize the yield of the major oligosaccharide (approximately 70% conversion of polysaccharide to oligosaccharide), a 4 day exposure of polysaccharide to HF was required (FIG. 4J).

Extending the exposure to 6 days resulted in increased internal hydrolysis of the major oligosaccharide (FIG. 4K). Interestingly, the polysaccharide was resistant to hydrolysis by 2N sulfuric acid for periods up to 8 h at a temperature of 100° C. (not shown). The relative ease with which HF released the oligomeric product from the purified polysaccharide as well as the resistance to hydrolysis by sulfuric acid suggested that the constituent oligosaccharide was coupled by phosphodiester bonds. The rapidly migrating components seen on HPTLC plates (FIG. 4, lanes G-K) appear derived from the major oligosaccharide since the HPLC purified oligosaccharide (FIG. 4L) yielded identical products when treated with HF (4d, 4° C.) (FIG. 4M). The most rapidly migrating component appears to be free rhamnose.

Composition of the oligosaccharide. Gas-liquid chromatographic analysis of the alditol acetate derivatives of the TFA hydrolyzed oligosaccharide verified the putative carbohydrate composition deduced by HPTLC. The oligosaccharide was found to contain rhamnose, galactose and glucose in the approximate molar ratios of 2:3:1, respectively (rhamnose 1.56-2.10: galactose 3: glucose 0.86-1.38). Analysis of the alditol acetate derivatives of the material collected as Peak 2a and 2b material (see FIG. 1) revealed that they were essentially identical indicating that the peak contained a single polysaccharide. Polysaccharide purified from autoclaving extract gave similar molar ratios for rhamnose, galactose and glucose (data not shown).

Figure 5:
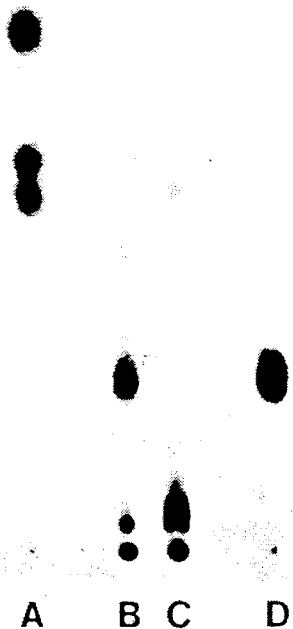
FIGURE 5. HPTLC of mutanolysin-released, HF treated (4d, 4° C.), polysaccharide material from coaggregation-deficient mutant S. oralis PK1831 and wild type S. oralis H1. B) Wild type mutanolysin-released material and HF treatment; C) Mutant mutanolysin-released material after HF treatment. Standards A) Equimolar mixture of rhamnose, glucose and galactose; D) HPLC purified oligosaccharide of wild type origin.

Comparative studies with a coaggregation-defective mutant. A coaggregation-defective mutant, S. oralis PK1831, derived from S. oralis H1 was examined for the presence of a polysaccharide structurally related to the CIP and an oligosaccharide similar or identical to that isolated from wild type S. oralis H1. Cells of the mutant were grown and processed under conditions identical to those used with wild type cells. The properties of the mutanolysin released polysaccharide material from the coaggregation defective mutant of S. oralis H1 were very different from CIP, i.e., this material failed to bind to the anion exchange column, it failed to block coaggregation, and treatment with HF did not yield the coaggregation-inhibiting oligosaccharide similar to that isolated from wild type cells (FIG. 5). This finding supports the finding according to the instant invention, i.e., that the hexasaccharide is the determining factor in the coaggregation inhibiting activity, or, in other words, that the hexasaccharide repeating unit derived from the CIP purified from the wild type Streptococcus oralis H1 cell functions as the receptor for the adhesin from Capnocytophaga ochracea ATCC 33596.

Figure 6:
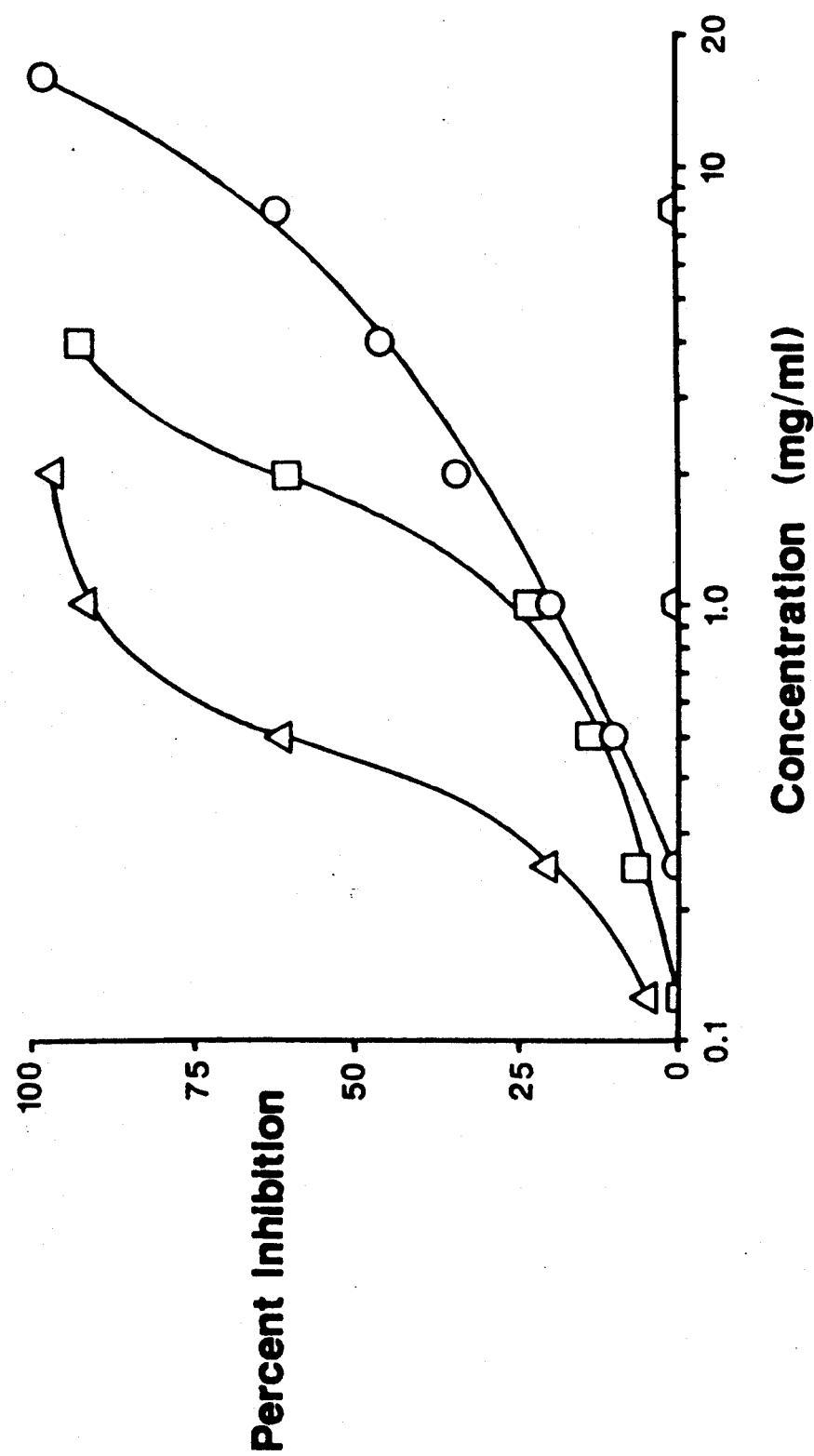
FIG. 6. Quantitative inhibition of coaggregation between S. oralis H1 and C. ochracea ATCC 33596 with S. oralis H1 cell wall mutanolysin extract (◯), purified CIP (▢), and purified oligosaccharide (△). 50% inhibition concentrations for the mutanolysin-released material, the purified polysaccharide and the purified oligosaccharide were 5.10, 1.79 and 0.44 mg/ml respectively.

Quantitative inhibition assays. Quantitative inhibition assays (FIG. 6) were performed with mutanolysin extract, polysaccharide purified by ion exchange (from pooled Peak 2, FIG. 1) and HPLC purified oligosaccharide (see FIG. 2). These moieties produced a 50% inhibition of coaggregation at concentrations of 5.10, 1.79 and 0.44 mg/ml respectively. The free oligosaccharide was therefore the most efficient inhibitor of Capnocytophaga ochracea ATCC 33596- Streotococcus oralis H1 coaggregation, as it was 4 times more effective than the mutanolysin-released material. Oxidation of the purified polysaccharide with periodate destroyed all coaggregation-inhibiting activity.

REFERENCES

1. Ames, B.N. 1966. Assay of inorganic phosphate, total phosphate and phosphatases. Meth. Enzy. s: 115-118.
2. Bradford, M. 1978. A rapid and sensitive method for the quantitation of microgram quantities of protein utilizing the principle of protein-dye binding. Anal. Biochem., 7z: 248-254.
3. Campbell, L.K., K.W. Knox, and A.L. Wicken. 1978. Extractability of cell wall polysaccharide from lactobacilli and streptococci by autoclaving and by dilute acid. Infec. Immun. 22: 42-851.
4. Carlsson, J., H. Grahnen, G. Jonsson and S. Wikner. 1970. Establishment of Streptococcus sanguis in the mouth of infants. Arch. Oral Biol. 15: 1143-1148.
5. Cisar, J.O., P.E. Kolenbrander and F.C. McIntire. 1979. Specificity of coaggregation reactions between human oral Streptocci and strains of Actinomyces viscosus or Actinomyces naeslundi. Infect. Immun. 24: 742-752.
6. Cisar, J., M.J. Brennan and A.L. Sandberg. 1985. Lectin-specific interaction of Actinomyces Streptococci with oral Streptocci. In S.E. Mergenhagen and B. Rosan. (ed.), Molecular basis of oral microbial adhesin. Amer. Soc. Microb., Washington, D.C.
7. Dubois, M., K.A. Gilles, J.K. Hamilton, P.A. Rebers and F. Smith. 1956. Colorimetric determination of sugars and related substances. Anal. Chem. 28: 350-356.
8. Fox, A., S.L. Morgan, J.R. Hudson, Z.T. Zhu and p.Y. Lau. 1983. Capillary gas chromatographic analysis of alditol acetates of neutral and amino sugars in bacterial cell walls. J. Chrom. 256: 429-438.
9. Kolenbrander, P.E. and R.N. Andersen. 1984. Cell to cell interactions of Capnocytophaga and Bacteroides species with other oral bacteria and their potential role in the development of plaque. J. Periodont. Res. 19: 564-569.
10. Kolenbrander, P.E. 198S. Intergeneric coaggregation among human oral bacteria and ecology of dental plaque. Annu. Rev. Microbiol. 42:627-56.
11. Kolenbrander, P.E. 1989. Surface recognition among oral bacteria: multigeneric coaggregates and their mediators. CRC Crit. Rev. Microbiol. In press.
12. Lato, M., B. Brunelli, G. Giuffini and T. Mezzetti. 1968. Analysis of carbohydrates in biological fluids by means of thin layer chromatography. J. Chromatog. 36 191-197.
13. McIntire, F.C., A.E. vatter, J. Baros and J. Arnold. 1978. Mechanism of coaggregation between Actinomyces viscosus T14V and Streptococcus sanguis 34. Infect. Immun. 21: 978-988.
14. McIntire, F.C. 1985. Specific surface components and microbial coaggregation. In S.E. Mercenhaqen and B. Rosan (ed.), Molecular basis of oral microbial adhesin. Amer. Soc. Microb., Washington, D.C.
15. McIntire, F.C., C.A. Bush, S-S. Wu, S-C. Li, Y-T. Li, M. McNeil, S.S. Tjoa and P.V. Fennessey. 1987. Structure of a new hexasaccharide from the coaggregation polysaccharide of Streptococcus sanguis 34. McIntire. Res. 166: 133-143.
16. Mcintire, F.C. L.K. Crosby, A.E. Vatter, J.O. Cisar, M.R. McNeil, C.A. Bush, S.S. Tjoa, and P.V. Fennessey. 1988. A cell wall polysaccharide from Streotococcus sanquis 34 that inhibits coaggregation of this organism with Actinomyces viscosus T14V. J. Bact. 170 : 2229-2235.

17. Maryanski, J.H. and C.L. wittenberger. 1975. Mannitol transport in *Streptococcus mutans*. J. Bacteriol. 124: 1475-81.
18. Schiffman, G., E.A. Kabat and W. Thompson. 1964. Immunochemical studies on blood groups XXX. Cleavage of A, B and H blood group substances by alkali. Biochem. 3: 113-120.
19. Socransky, S.S., A.D. Manganiello, D. Propas, v. oram and J. van Houte. 1977. Bacteriological studies of developing supragingival dental plaque. J. Periodontal Res. 12: 90-106.
20. Wang, A-C. 1982. Methods of immune diffusion, immunoelectrophoresis, precipitation, and agglutination. In J.J. Marchalonis and G.W. Warr (ed.), Antibody as a tool: the applications of immunochemistry. Wiley, N.Y.
21. Warren, C.D., A.S. Scott and R.W. Jeanloz. 1983. Chromatographic separation of oligosaccharides from mannosidosis urine. Mcintire. Res. 116: 171-182.
22. Weiss, E.I., J. London, P.E. Kolenbrander, A.S. Kagermeier and R.N. Andersen. 1987. Characterization of lectinlike surface components on *Capnocytophaga ochracea* ATCC 33596 that mediate coaggregation with gram-positive oral bacteria. Infect. Immun. 55: 1198-1202.
23. prehm, P., S. Stirm, B. Jann and K. Jann. 1975. Cell-wall lipopolysaccharide from *Escherichia coli*. B. Eur. J. Biochem. 56: 41-55.
24. Mellis, S.J., and J.V. Baenzinger. 1981. Separation of neutral oligosaccharides by high-performance liquid chromatography. Anal. Biochem. 114: 276-280.

What is claimed is:

1. A method of inhibiting the build up of human dental plaque deposits in the human oral cavity by administering a composition comprising the hexasaccharide of the formula I

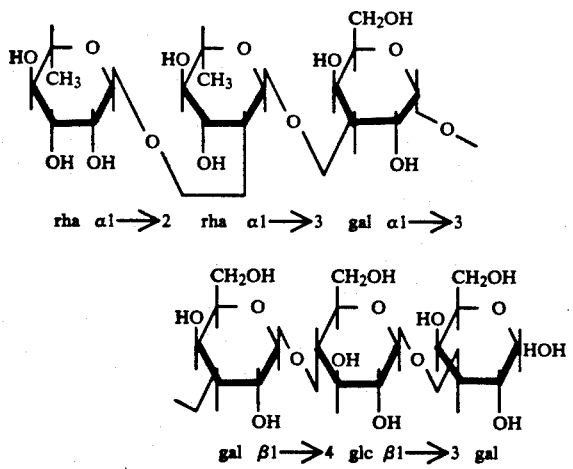

wherein "rha" designates rhamnose, "gal" designates galactose, and "glc" designates glucose, to the human oral cavity.

2. A composition for inhibiting the build of human dental plaque deposits in the human oral cavity comprising the hexasaccharide of the formula I

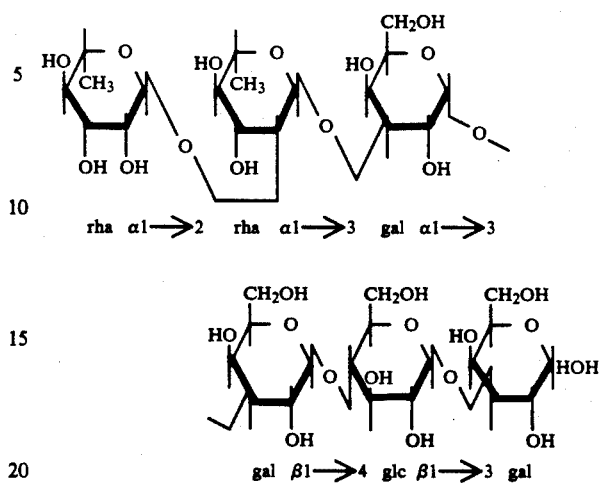

wherein "rha" designates rhamnose, "gal" designates galactose, and "glc" designates glucose, in admixture with a conventional carrier or diluent for oral hygiene products.

3. A composition according to claim 2 in the form of a tooth paste or mouth wash.

4. A composition according to claim 2 wherein the hexasaccharide is present in an amount of from 0.001 to 5% by weight.

5. A method of inhibiting coaggregation between *Streptococcus oralis* ATCC 55229 and *Capnocytophaga ochracea* ATCC 33596 wherein the hexasaccharide of the formula I

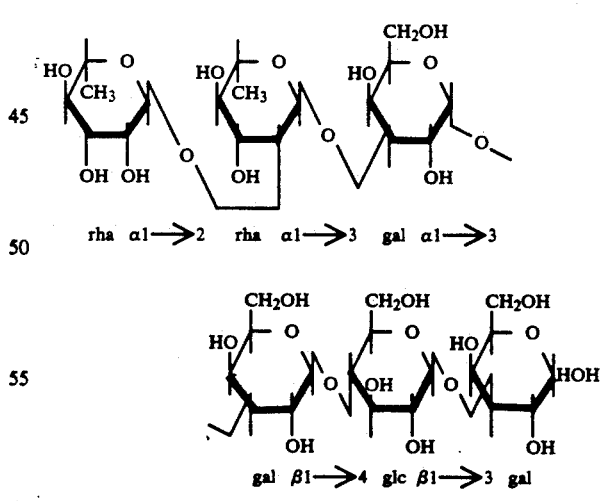

wherein "rha" designates rhamnose, "gal" designates galactose, and "glc" designates glucose, is preincubated with the *Capnocytophaga ochracea*.

6. A method for inhibiting the adhesin from the gram-negative bacteria *Capnocytophaga ochracea* ATCC 33596 wherein the hexasaccharide of the formula I

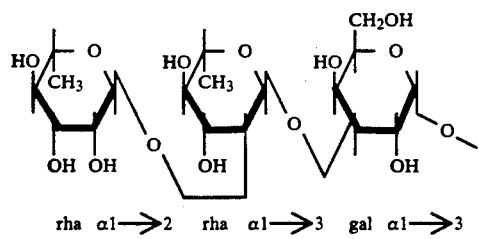
rha α1→2  rha α1→3  gal α1→3
-continued
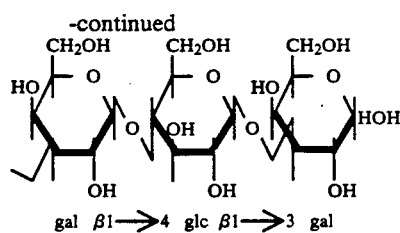
gal β1→4  glc β1→3  gal
wherein "rha" designates rhamnose, "gal" designates galactose, and "glc" designates glucose, is incubated with the bacteria.
* * * * *